(12) United States Patent
Inomata et al.

(10) Patent No.: US 11,766,852 B2
(45) Date of Patent: Sep. 26, 2023

(54) COMPOSITION FOR INSERTION AUXILIARY TUBE, INSERTION AUXILIARY TUBE, SET OF INSERTION AUXILIARY TUBE AND ENDOSCOPE, ENDOSCOPE APPARATUS, AND METHOD FOR PRODUCING INSERTION AUXILIARY TUBE

(71) Applicant: FUJIFILM Corporation, Tokyo (JP)

(72) Inventors: Sotaro Inomata, Ashigarakami-gun (JP); Nobuharu Takahashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 308 days.

(21) Appl. No.: 17/147,651

(22) Filed: Jan. 13, 2021

(65) Prior Publication Data

US 2021/0129510 A1 May 6, 2021

Related U.S. Application Data

(63) Continuation of application No. PCT/JP2019/028028, filed on Jul. 17, 2019.

(30) Foreign Application Priority Data

Jul. 17, 2018 (JP) ................................ 2018-134503

(51) Int. Cl.
*B32B 1/08* (2006.01)
*B32B 27/28* (2006.01)
(Continued)

(52) U.S. Cl.
CPC ........ *B32B 27/283* (2013.01); *A61B 1/00135* (2013.01); *B32B 1/08* (2013.01);
(Continued)

(58) Field of Classification Search
CPC ......... B32B 27/283; B32B 1/08; B32B 27/08; B32B 27/26; B32B 27/302; B32B 27/308;
(Continued)

(56) References Cited

U.S. PATENT DOCUMENTS

2002/0161065 A1  10/2002  DiTizio et al.
2004/0086568 A1  5/2004   Ditizio et al.
(Continued)

FOREIGN PATENT DOCUMENTS

EP   3 824 915 A1    5/2021
JP   2004-524903 A   8/2004
(Continued)

OTHER PUBLICATIONS

Notice of Reasons for Refusal dated Apr. 26, 2022 from the Japanese Patent Office in corresponding Japanese Application No. 2020-531331.
(Continued)

*Primary Examiner* — Michael B Nelson
(74) *Attorney, Agent, or Firm* — Sughrue Mion, PLLC (57) ABSTRACT

There is provided an insertion auxiliary tube having a tubular substrate a and a layer b disposed on at least one of an inside or an outside of the tubular substrate a. The layer b includes a polymer including a polysiloxane structure. The polymer includes an acrylic acid component, an acrylic acid ester component, an acrylamide component, or a styrene component and has a particular polar group in a molecule thereof. There are also provided a composition for an insertion auxiliary tube capable of providing the insertion auxiliary tube, a set of the insertion auxiliary tube and an endoscope, an endoscope apparatus including the insertion auxiliary tube and an endoscope, and a method for producing the insertion auxiliary tube.

15 Claims, 1 Drawing Sheet

(51) Int. Cl.
| | |
|---|---|
| *A61B 1/00* | (2006.01) |
| *B32B 27/08* | (2006.01) |
| *B32B 27/26* | (2006.01) |
| *B32B 27/30* | (2006.01) |
| *B32B 27/34* | (2006.01) |
| *B32B 27/36* | (2006.01) |
| *B32B 27/40* | (2006.01) |

(52) U.S. Cl.
CPC .............. *B32B 27/08* (2013.01); *B32B 27/26* (2013.01); *B32B 27/302* (2013.01); *B32B 27/308* (2013.01); *B32B 27/34* (2013.01); *B32B 27/36* (2013.01); *B32B 27/40* (2013.01); *B32B 2250/02* (2013.01); *B32B 2250/03* (2013.01); *B32B 2250/24* (2013.01); *B32B 2307/746* (2013.01); *B32B 2325/00* (2013.01); *B32B 2333/08* (2013.01); *B32B 2375/00* (2013.01); *B32B 2377/00* (2013.01); *B32B 2383/00* (2013.01); *B32B 2535/00* (2013.01)

(58) Field of Classification Search
CPC ......... B32B 27/34; B32B 27/36; B32B 27/40; B32B 2250/02; B32B 2250/03; B32B 2250/24; B32B 2307/746; B32B 2325/00; B32B 2333/08; B32B 2375/00; B32B 2377/00; B32B 2383/00; B32B 2535/00; A61B 1/00135; A61B 1/0011; A61B 1/00154; C08F 283/12; C08F 283/124; C09D 151/085; G02B 23/2476; A61L 29/14; A61L 2400/10; A61L 29/085; C08G 77/442

See application file for complete search history.

(56) References Cited

U.S. PATENT DOCUMENTS

| | | |
|---|---|---|
| 2008/0255417 A1 | 10/2008 | Bob |
| 2010/0094086 A1 | 4/2010 | Konstantin |
| 2010/0280146 A1* | 11/2010 | Vanderlaan .............. A61L 27/26 264/2.6 |
| 2012/0220689 A1* | 8/2012 | Yao ......................... G02B 1/043 53/425 |
| 2017/0204213 A1* | 7/2017 | Kato ....................... A61L 27/52 |
| 2017/0360994 A1* | 12/2017 | Havenstrite ........... A61L 29/085 |
| 2019/0328931 A1 | 10/2019 | Inomata et al. |

FOREIGN PATENT DOCUMENTS

| | | |
|---|---|---|
| JP | 2004-528418 A | 9/2004 |
| JP | 2008-259856 A | 10/2008 |
| JP | 2010-5293 A | 1/2010 |
| JP | 2010-88894 A | 4/2010 |
| WO | 2016/200337 A1 | 12/2016 |
| WO | 2018/131518 A1 | 7/2018 |

OTHER PUBLICATIONS

Notice of Reasons for Refusal dated Oct. 5, 2021 by the Japanese Patent Office in corresponding Japanese Application No. 2020-531331.
Extended European Search Report dated Aug. 2, 2021 in corresponding European Application No. 19837458.9.
Office Action dated Sep. 20, 2022 issued by the Japanese Patent Office in corresponding Japanese Application No. 2020-531331.
International Search Report dated Oct. 15, 2019 from the International Searching Authority in International Application No. PCT/JP2019/028028.
Written Opinion dated Oct. 15, 2019 from the International Bureau in International Application No. PCT/JP2019/028028.
International Preliminary Report on Patentability dated Jan. 19, 2021 from the International Bureau in International Application No. PCT/JP2019/028028.
Office Action dated Feb. 21, 2023 issued by the Japanese Patent Office in Japanese Application No. 2020-531331.

* cited by examiner

COMPOSITION FOR INSERTION AUXILIARY TUBE, INSERTION AUXILIARY TUBE, SET OF INSERTION AUXILIARY TUBE AND ENDOSCOPE, ENDOSCOPE APPARATUS, AND METHOD FOR PRODUCING INSERTION AUXILIARY TUBE

CROSS-REFERENCE TO RELATED APPLICATIONS

This application is a Continuation of PCT International Application No. PCT/JP2019/028028 filed on Jul. 17, 2019, which claims priority under 35 U.S.C. § 119 (a) to Japanese Patent Application No. 2018-134503 filed in Japan on Jul. 17, 2018. Each of the above applications is hereby expressly incorporated by reference, in its entirety, into the present application.

BACKGROUND OF THE INVENTION

1. Field of the Invention

The present invention relates to a composition for an insertion auxiliary tube, an insertion auxiliary tube, a set of an insertion auxiliary tube and an endoscope, an endoscope apparatus, and a method for producing the insertion auxiliary tube.

2. Description of the Related Art

In treatment using an endoscope, an insertion part of an endoscope is inserted into a body cavity, an observation target such as an inner wall of an organ or an affected part such as a tumor (hereafter, the observation target and the affected part are collectively referred to as an "affected part or the like") is imaged to obtain information of the affected part or the like, and a treatment tool such as forceps or an injection needle is taken out from a forceps port disposed at a distal end of the insertion part as necessary to remove the affected part or the like.

The insertion part of the endoscope desirably does not damage an organ and does not cause pain and discomfort to a patient. In view of such a demand, a spiral tube formed by spirally winding a soft bendable metal strip is employed as a flexible tube constituting the insertion part of the endoscope, and the insertion part of the endoscope has flexibility.

In order to smoothly and reliably cause such a flexible insertion part of the endoscope to reach an affected part or the like from the mouth or the anus, a tube (hereafter also referred to as an "insertion auxiliary tube") is used to assist operations such as insertion of the insertion part of the endoscope into a body cavity and movement of the insertion part in a body cavity. For example, JP2004-524903A describes a colonic overtube having a proximal end disposed outside the colon, a distal end inserted into the colon, and a colonoscope lumen extending inside the overtube. At least part of the colonic overtube is flexible in a lateral direction. The colonic overtube can be easily bent without being substantially twisted during forward movement.

SUMMARY OF THE INVENTION

An endoscope is used by being slid in a body cavity, and therefore it is important to improve the slidability of an outer surface of the insertion auxiliary tube that comes into contact with a tissue in a body cavity. Furthermore, an insertion auxiliary tube is inserted into a body cavity, and an endoscope is inserted into the tube while water is being passed through the tube to observe the inside of the body cavity or to take a biopsy. Therefore, it is also important to improve the slidability of the inner surface of the insertion auxiliary tube.

JP2004-524903A discloses that a lubricating layer formed of, for example, a gel of silicone or polytetrafluoroethylene (PTFE) is disposed on one of the inner surface and the outer surface of the colonic overtube in order to improve the slidability. However, when the colonic overtube is left while being bent with a large curvature in a body cavity, the lubricating layer may peel off or become cracked.

It is an object of the present invention to provide a composition for an insertion auxiliary tube capable of providing an insertion auxiliary tube in which a lubricating layer disposed on the surface of a tubular substrate is less likely to peel off and cracking is less likely to occur in the lubricating layer even if the insertion auxiliary tube is left while being bent with a large curvature. It is another object of the present invention to provide an insertion auxiliary tube in which a lubricating layer disposed on the surface of a tubular substrate is less likely to peel off and cracking is less likely to occur in the lubricating layer even if the insertion auxiliary tube is left while being bent with a large curvature. It is another object of the present invention to provide a set of the insertion auxiliary tube and an endoscope. It is another object of the present invention to provide an endoscope apparatus including the insertion auxiliary tube and an endoscope. It is another object of the present invention to provide a method for producing the insertion auxiliary tube.

The above objects have been achieved by the following means.

<1>

A composition for an insertion auxiliary tube includes a polymer including a polysiloxane structure.

The polymer includes at least one of an acrylic acid component, an acrylic acid ester component, an acrylamide component, or a styrene component as a constituent component, and has at least one of a hydroxy group, a carboxy group, an amino group, an isocyanate group, an oxazolinyl group, an epoxy group, a sulfanyl group, an azide group, a trialkoxysilyl group, or an acid anhydride structure in a molecule thereof.

<2>

An insertion auxiliary tube has a tubular substrate a and a layer b disposed on at least one of an inside or an outside of the tubular substrate a.

The layer b includes a polymer including a polysiloxane structure.

The polymer includes at least one of an acrylic acid component, an acrylic acid ester component, an acrylamide component, or a styrene component as a constituent component, and has at least one of a hydroxy group, a carboxy group, an amino group, an isocyanate group, an oxazolinyl group, an epoxy group, a sulfanyl group, an azide group, a trialkoxysilyl group, or an acid anhydride structure in a molecule thereof.

<3>

In the insertion auxiliary tube according to <2>, the polymer is a graft polymer having the polysiloxane structure in a graft chain.

<4>

In the insertion auxiliary tube according to <2> or <3>, the polymer includes a structural unit represented by formula (1) below and includes at least one of a structural unit represented by formula (2) below, a structural unit represented by formula (3) below, or a structural unit represented by formula (4) below.

Formula (1)

In the formula, $R^1$ to $R^6$ represent a hydrogen atom or an organic group. $L^1$ represents a single bond or a divalent linking group, and n1 represents 3 to 10,000.

Formula (2)

In the formula, $R^7$ and $R^a$ represent a hydrogen atom or an organic group.

Formula (3)

In the formula, $R^8$, $R^{b1}$, and $R^{b2}$ represent a hydrogen atom or an organic group.

Formula (4)

In the formula, $R^9$ represents a hydrogen atom or an organic group. $R^{c1}$ to $R^{c5}$ represent a hydrogen atom, a halogen atom, or an organic group.

<5>

In the insertion auxiliary tube according to <4>, $R^a$ represents a group represented by formula (5) below or a nitrogen-containing organic group.

Formula (5)

In the formula, n2 represents 1 to 10,000. $R^{10}$ represents a hydrogen atom or an organic group. * represents a direct bond.

<6>

In the insertion auxiliary tube according to <4> or <5>, n1 represents 135 to 10,000.

<7>

In the insertion auxiliary tube according to any one of <2> to <6>, the polymer of the layer b is a crosslinked body, and the crosslinked body has a crosslinked structure constituted by at least one of a crosslinking agent component derived from a structural unit represented by formula (6) below or a crosslinking agent component derived from a compound represented by formula (7) below, Formula (6)

Formula (7)

In the formula, $R^{11}$ represents a hydrogen atom or an organic group. X represents a hydroxy group, a carboxy group, an amino group, an isocyanate group, an oxazolinyl group, an epoxy group, a vinyl group, an ethynyl group, a sulfanyl group, an azide group, a trialkoxysilyl group, or a group having an acid anhydride structure.

Y represents an m-valent linking group, and m represents an integer of 2 or more. $R^{dm}$ has the same definition as X.

<8>

In the insertion auxiliary tube according to <7>, a content of the crosslinking agent component in the crosslinked body of the layer b is 30 to 90 mass %.

<9>

In the insertion auxiliary tube according to any one of <2> to <8>, a surface of the layer b on an opposite side with respect to the tubular substrate a is subjected to hydrophilic treatment.

<10>

In the insertion auxiliary tube according to any one of <2> to <9>, the tubular substrate a is formed of at least one of a urethane resin, a silicone resin, a fluorocarbon resin, an olefin resin, or an acrylic resin.

<11>

In the insertion auxiliary tube according to any one of <2> to <10>, the tubular substrate a is formed of a silicone resin.

<12>

In the insertion auxiliary tube according to any one of <2> to <11>, the tubular substrate a has a Shore A hardness of A40 or more and less than A95.

<13>

The insertion auxiliary tube according to any one of <2> to <12> has a layer c disposed on the layer b and including a hydrophilic polymer.

<14>

The insertion auxiliary tube according to any one of <2> to <13> has a Shore A hardness of A40 or more and less than A95.

<15>

The insertion auxiliary tube according to any one of <2> to <14> includes an inflatable and deflatable balloon on an outer surface of a distal end thereof.

<16>

The insertion auxiliary tube according to any one of <2> to <15> has an outer diameter of ϕ7 to 20 mm.

<17>

The insertion auxiliary tube according to any one of <2> to <16> is an insertion auxiliary tube of an endoscope.

<18>

A set of the insertion auxiliary tube according to <17> and an endoscope.

<19>

In the set according to <18>, the insertion auxiliary tube has a smaller length than an insertion part of the endoscope, and a difference in length between the insertion auxiliary tube and the insertion part of the endoscope is 200 to 800 mm.

<20>

An endoscope apparatus includes the insertion auxiliary tube according to <17> and an endoscope.

<21>

In the endoscope apparatus according to <20>, the insertion auxiliary tube has a smaller length than an insertion part of the endoscope, and a difference in length between the insertion auxiliary tube and the insertion part of the endoscope is 200 to 800 mm.

<22>

In the endoscope apparatus according to <20> or <21>, the endoscope is inserted into a body cavity by rotating the insertion auxiliary tube.

<23>

A method for producing the insertion auxiliary tube according to any one of <2> to <17> includes a step of applying, onto a tubular substrate, a composition that includes a polymer including a polysiloxane structure and that includes an organic solvent.

The polymer includes at least one of an acrylic acid component, an acrylic acid ester component, an acrylamide component, or a styrene component as a constituent component, and has at least one of a hydroxy group, a carboxy group, an amino group, an isocyanate group, an oxazolinyl group, an epoxy group, a sulfanyl group, an azide group, a trialkoxysilyl group, or an acid anhydride structure in a molecule thereof.

In this specification, every numerical range expressed using "to" means a range including numerical values before and after "to" as the lower and upper limits.

In this specification, when a plurality of substituents, linking groups, or structural units are represented by a particular symbol (hereafter referred to as substituents and the like) or when a plurality of substituents and the like are simultaneously or alternatively defined, the substituents and the like may be the same as or different from each other. The same also applies to the definition of the number of substituents and the like. When a plurality of substituents and the like are close (particularly adjacent) to each other, they may be linked or fused to each other to form a ring. In a polymer having a plurality of structural units having substituents or linking groups represented by a particular symbol, the plurality of structural units may be the same as or different from each other.

In this specification, unless otherwise specified, the form of polymers is not particularly limited, and may be any form such as random, block, or graft as long as the effects of the present invention are not impaired.

In this specification, the terminal structure of polymers is not particularly limited. The terminal structure is appropriately determined in accordance with the type of substrate used during synthesis, the type of quenching agent (reaction terminator) during synthesis, and the like, and is not uniquely determined. Examples of the terminal structure include a hydrogen atom, a hydroxy group, a halogen atom, an ethylenically unsaturated group, and an alkyl group.

In this specification, the terms "acrylic acid", "acrylamide", and "styrene" are used in a broader sense than usual.

That is, the term "acrylic acid" refers to all compounds having a structure of $R^A$—$C(=CR^B{}_2)COOH$ ($R^A$ and $R^B$ each independently represent a hydrogen atom or a substituent).

The term "acrylamide" refers to all compounds having a structure of $R^C$—$C(=CR^D{}_2)CONR^E{}_2$ ($R^C$, $R^D$, and $R^E$ each independently represent a hydrogen atom or a substituent).

The term "styrene" refers to all compounds having a structure of $R^F$—$C(=CR^G{}_2)C_6R^H{}_6$ ($R^F$, $R^G$, and $R^H$ each independently represent a hydrogen atom or a substituent).

In this specification, when the number of carbon atoms of a certain group is specified, the number of carbon atoms means the number of carbon atoms of the entire group. That is, in the case where the group further has a substituent, the number of carbon atoms means the total number of carbon atoms of the group including the substituent.

In this specification, the weight-average molecular weight (Mw) and the number-average molecular weight (Mn) can be measured as molecular weights in terms of polystyrene by gel permeation chromatography (GPC) unless otherwise specified. At this time, the GPC instrument is HLC-8220 (manufactured by Tosoh Corporation), the column is G3000HXL+G2000HXL (both are TSK-gel HXL (trade name) series manufactured by Tosoh Corporation), the flow rate is 1 mL/min at 23° C., and detection is performed by using refractive index (RI). The eluant can be selected from the group consisting of THF (tetrahydrofuran) chloroform. NMP (N-methyl-2-pyrrolidone), and m-cresol/chloroform (manufactured by Shonan Wako Pure Chemical Industries, Ltd.), and THF is used as long as the target material is dissolved in THF.

In the measurement of the molecular weight of a polymer used in a hydrophilic coating layer, N-methyl-2-pyrrolidone (manufactured by Wako Pure Chemical Industries, Ltd.) is used as an eluant, and TSK-gel Super AWM-H (trade name) manufactured by Tosoh Corporation is used as a column.

Even if the insertion auxiliary tube according to an embodiment of the present invention is left while being bent with a large curvature, the lubricating layer disposed on the surface of the tubular substrate is less likely to peel off, and cracking is less likely to occur in the lubricating layer. The composition for an insertion auxiliary tube according to an embodiment of the present invention can provide the above insertion auxiliary tube. According to the present invention, there can be provided a set of the insertion auxiliary tube and an endoscope, and an endoscope apparatus including the insertion auxiliary tube and an endoscope. According to the method of producing an insertion auxiliary tube according to an embodiment of the present invention, the insertion auxiliary tube can be obtained.

DESCRIPTION OF THE PREFERRED EMBODIMENTS

The composition for an insertion auxiliary tube according to an embodiment of the present invention (hereafter also referred to as a "composition according to an embodiment of the present invention") includes a polymer including a polysiloxane structure and can be suitably used for producing the insertion auxiliary tube according to an embodiment of the present invention.

Composition According to Embodiment of the Present Invention

The composition according to an embodiment of the present invention includes a polymer including a polysiloxane structure. The polymer includes at least one of an acrylic acid component, an acrylic acid ester component, an acrylamide component, or a styrene component as a constituent component, and has at least one of a hydroxy group, a carboxy group, an amino group, an isocyanate group, an oxazolinyl group, an epoxy group, a sulfanyl group, an azide group, a trialkoxysilyl group, or an acid anhydride structure in its molecule.

The composition according to an embodiment of the present invention may include a solvent.

Examples of the solvent included in the composition according to an embodiment of the present invention include ether solvents such as dibutyl ether, dimethoxymethane, dimethoxyethane, diethoxyethane, propylene oxide, 1,4-dioxane, 1,3-dioxolane, 1,3,5-trioxane, tetrahydrofuran, anisole, and phenetole; ketone solvents such as acetone, methyl ethyl ketone, diethyl ketone, dipropyl ketone, diisobutyl ketone, methyl isobutyl ketone, cyclopentanone, cyclohexanone, methylcyclohexanone, and dimethylcyclohexanone; ester solvents such as ethyl formate, propyl formate, n-pentyl formate, methyl acetate, ethyl acetate, methyl propionate, ethyl propionate, n-pentyl acetate, and γ-butyrolactone; alcohol solvents such as methanol, ethanol, 1-propanol, 2-propanol (isopropyl alcohol), 1-butanol, 2-butanol, tert-butanol, 1-pentanol, 2-methyl-2-butanol, and cyclohexanol; aromatic hydrocarbons such as xylene and toluene; halogenated hydrocarbon solvents such as methylene chloride, chloroform, and 1,1-dichloroethane; amide-based solvents such as N-methyl-2-pyrrolidone (NMP), N,N-dimethylformamide (DMF), and N,N-dimethylacetamide (DMAc); nitrile solvents such as acetonitrile; and organic solvents having two or more functional groups, such as methyl 2-methoxyacetate, methyl 2-ethoxyacetate, ethyl 2-ethoxyacetate, ethyl 2-ethoxypropionate, 2-methoxyethanol, 2-propoxyethanol, 2-butoxyethanol, 1,2-diacetoxyacetone, acetylacetone, diacetone alcohol, methyl acetoacetate, N-methylpyrrolidone, propylene glycol monomethyl ether acetate, and ethyl acetoacetate.

When the composition according to an embodiment of the present invention includes a solvent, the content of the solvent in the composition is preferably 60 to 99 mass %, more preferably 70 to 99 mass %, and further preferably 80 to 99 mass %.

The solid content (content ratio) of components other than the solvent included in the composition according to an embodiment of the present invention is as described in the insertion auxiliary tube according to an embodiment of the present invention. The solid content of components other than the solvent refers to a content of components other than a solvent remaining in a layer b when the layer b is provided.

When the composition according to an embodiment of the present invention includes a crosslinking agent described later, the composition is preferably stored at, for example, 20° C. to 40° C. with light shielding as necessary in order to suppress the progress of a crosslinking reaction until use.

Hereafter, preferred embodiments of the insertion auxiliary tube according to an embodiment of the present invention will be described.

Insertion Auxiliary Tube According to Embodiment of the Present Invention

Figure 1:
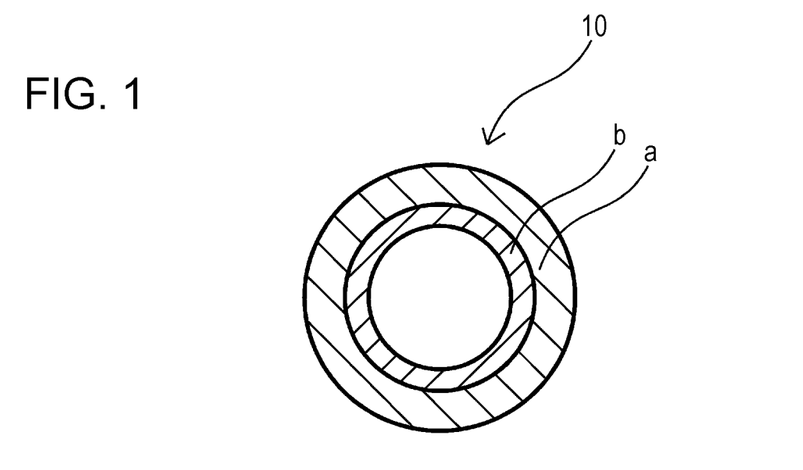
FIG. 1 is a sectional view illustrating an insertion auxiliary tube according to an embodiment of the present invention.

The insertion auxiliary tube according to an embodiment of the present invention can be used to assist insertion of an endoscope into a body cavity and movement of the endoscope in the body cavity. The insertion auxiliary tube can also be used as a medical tube such as a catheter. The insertion auxiliary tube according to an embodiment of the present invention is a laminated body having a tubular substrate (hereafter also referred to as a "tubular substrate a") and a layer (hereafter also referred to as a "layer b") disposed on at least one of the inside or the outside of the tubular substrate a and including a polymer including a polysiloxane structure described later. Although an interlayer may be provided between the layer b and the substrate a, the layer b is preferably disposed directly on the substrate a as illustrated in FIG. 1.

Hereafter, the layer b may be referred to as a lubricating layer. When a layer c described later is disposed on the layer b, the layer b and the layer c together constitute a lubricating layer.

Tubular Substrate a

The material for the tubular substrate a constituting the insertion auxiliary tube according to an embodiment of the present invention is not particularly limited. Materials that can be used for medical devices and the like can be widely employed. For example, glass, plastic, metal, ceramic, fiber, fabric, paper, leather, synthetic resin, and combinations thereof can be used in accordance with the purpose. In particular, the tubular substrate a is preferably formed of a resin.

The tubular substrate a can be suitably used in the present invention even if a surface on which the layer b is to be formed has a low surface free energy. For example, the surface free energy of the surface of the tubular substrate a on which the layer b is to be formed can be set in the range of 5 to 1500 mN/m and can also be set in the range of 10 to 500 mN/m. The surface free energy of the surface of the tubular substrate a on which the layer b is to be formed may be 5 to 300 mN/m, 10 to 200 mN/m, or 10 to 100 mN/m and is also preferably 10 to 50 mN/m. Even when the surface free energy of the surface of the tubular substrate a on which the layer b is to be formed is low, the layer b can be formed on the tubular substrate a without causing cissing or unevenness because the layer b includes a particular polymer b described later.

The surface free energy can be measured by a typical method. That is, the contact angle of a film is measured with both water and diiodomethane, and is substituted into the following Owens formula (the following is a formula in the case where diiodomethane ($CH_2I_2$) is used as an organic solvent).

$$1+\cos\theta_{H2O}=2(\gamma_s^d)^{1/2}(\gamma_{H2O}^d)^{1/2}/\gamma_{H2O,V}+2(\gamma_s^h)^{1/2}(\gamma_{H2O}^h)^{1/2}/\gamma_{H2O,V}$$

$$1+\cos\theta_{CH2I2}=2(\gamma_s^d)^{1/2}(\gamma_{CH2I2}^d)^{1/2}/\gamma_{CH2I2,V}+2(\gamma_s^h)^{1/2}(\gamma_{CH2I2}^h)^{1/2}/\gamma_{CH2I2,V} \quad \text{Owens formula}$$

Herein, $\gamma_{H2O}^d=21.8$, $\gamma_{CH2I2}^d=49.5$, $\gamma_{H2O}^h=51.0$, $\gamma_{CH2I2}^h=1.3$, $\gamma_{H2O,V}=72.8$, and $\gamma_{CH2I2,V}=50.8$. When the measured contact angle of water is substituted into $\theta_{H2O}$ and the measured contact angle of diiodomethane is substituted into $\theta_{CH2I2}$, the dispersion force component $\gamma_S^d$ and the polar component $\gamma_S^h$ of the surface energy are determined, respectively. The sum $\gamma_S^{Vh} = \gamma_S^d + \gamma_S^h$ can be determined as a surface free energy (mN/m).

The contact angle is measured by setting the droplet volume to 1 μL for both pure water and diiodomethane and reading the contact angle ten seconds after the dropping. At this time, the measurement atmosphere is set to a temperature of 23° C. and a relative humidity of 50%.

The material for the tubular substrate a is, for example, suitably at least one of a urethane resin, a silicone resin, a fluorocarbon resin, an olefin resin, or an acrylic resin. From the viewpoint of use as a medical material, a silicone resin is preferably used.

Urethane Resin

The urethane resin that can be used as a material for the tubular substrate a is not particularly limited. In general, urethane resins are synthesized by addition polymerization of polyisocyanate and polyol. Examples of the urethane resins that can be used include aliphatic polyurethanes obtained by using an aliphatic isocyanate as a polyisocyanate raw material, aromatic polyurethanes obtained by using an aromatic isocyanate as a polyisocyanate raw material, and copolymers of such polyurethanes.

Furthermore, Pandex series (trade name, manufactured by DIC Corporation), V-Gran series, V-Top series, and DNT-urethane Smile Clean series (trade name, all manufactured by Dai Nippon Toryo Co., Ltd.) serving as urethane resin paints, Polyflex series (trade name, manufactured by DKS Co., Ltd.), Ti-Prene series (trade name, manufactured by Tigers Polymer Corporation). Tecoflex (registered trademark) series (Thermedics Inc.), Miractran series (trade name, manufactured by Nippon Miractran Company Limited), Pellethane series (trade name, manufactured by The Dow Chemical Company), and the like can also be used as the urethane resin.

Silicone Resin

The silicone resin that can be used as a material for the tubular substrate a is not particularly limited, and the silicone resin may be cured using a curing agent. The curing reaction may be a typical reaction. For example, an organo-hydrogenpolysiloxane and an organopolysiloxane having an ethylenic C=C double bond can be cured using a platinum catalyst. In the case of curing the silicone resin by peroxide crosslinking, a peroxide is used.

Furthermore, rubber compound KE series (trade name, manufactured by Shin-Etsu Chemical Co., Ltd.), ELASTO-SIL (registered trademark) series (manufactured by Wacker Asahikasei Silicone Co., Ltd.). SILASTIC (registered trademark) series (manufactured by Dow Corning Toray Co., Ltd.), TSE series (trade name, manufactured by Momentive Performance Materials Japan Co., Ltd.), and the like can be used as the silicone resin.

Fluorocarbon Resin

The fluorocarbon resin that can be used as a material for the tubular substrate a is not particularly limited. For example, polytetrafluoroethylene, polyvinyl fluoride, polyvinylidene fluoride, polytrifluoroethylene, and copolymers thereof can be used.

Furthermore. Teflon (registered trademark, manufactured by DUPONT), Polyflon and Neoflon series (trade name, manufactured by Daikin Industries, Ltd.). Fluon (registered trademark) series and Cytop (registered trademark) series (manufactured by AGC Inc.), Dyneon series (trade name, manufactured by 3M), and the like can also be used as the fluorocarbon resin.

Olefin Resin

The olefin resin that can be used as a material for the tubular substrate a is not particularly limited. For example, polyethylene, polypropylene, polybutene, polypentene, polycyclopentene, polymethylpentene, polystyrene, polybutadiene, polyisoprene, copolymers thereof, and natural rubber can be used. Furthermore, ARTON (registered trademark) series (manufactured by JSR Corporation), SURFLEN (registered trademark) series (manufactured by Mitsubishi Chemical Corporation), ZEONOR (registered trademark) series, ZEONEX (registered trademark)(each manufactured by Zeon Corporation), and the like can also be used as the olefin resin.

Acrylic Resin

The acrylic resin that can be used as a material for the tubular substrate a is not particularly limited. Examples of the acrylic resin include polymethyl methacrylate, polymethacrylic acid, polymethyl acrylate, polyacrylic acid, polyethyl methacrylate, polyethyl acrylate, and copolymers of the foregoing.

Acrylite Series, Acrypet Series, Acryplen Series (trade name, all manufactured by Mitsubishi Rayon Co., Ltd.), solvent-based acrylic resin for coating Acrydic Series (trade name, manufactured by DIC Corporation), Almatex (registered trademark, manufactured by Mitsui Chemicals, Inc.), Hitaloid (trade name, manufactured by Hitachi Chemical Company, Ltd.), and the like can also be used as the acrylic resin.

The hardness of the tubular substrate a is not particularly limited, but the Shore A hardness is preferably 35 or more and more preferably 40 or more. The upper limit is preferably less than 95 and more preferably 85 or less. By setting the hardness of the tubular substrate a within the above range, even when the insertion auxiliary tube is left while being bent with a large curvature, the lubricating layer is less likely to peel off from the tubular substrate a (the adhesiveness between the tubular substrate a and the lubricating layer is further improved) and cracking is less likely to occur in the lubricating layer.

The insertion auxiliary tube itself also preferably has a Shore A hardness within the above range.

Layer b

In the insertion auxiliary tube according to an embodiment of the present invention, the layer b includes a polymer including a polysiloxane structure (hereafter also referred to as a "polymer b"). When the polymer b has a polysiloxane structure, the affinity of the polymer b for the surface of the tubular substrate a can be increased even if the surface free energy of the tubular substrate a is low. Thus, a layer including the polymer b can be formed without causing cissing or unevenness.

The polymer b includes, as a constituent component, at least one of an acrylic acid component, an acrylic acid ester component, an acrylamide component, or a styrene component in addition to the component having a polysiloxane structure.

The polymer b has at least one of a hydroxy group, a carboxy group, an amino group, an isocyanate group, an oxazolinyl group (oxazolyl group), an epoxy group, a sulfanyl group, an azide group, a trialkoxysilyl group, or an acid anhydride structure in its molecule (hereafter, these groups and structures are also collectively referred to as a "reactive functional group" or simply a "reactive group"). These reactive functional groups can interact with or react with a hydrophilic polymer to be applied onto the layer b and described later to further enhance the adhesiveness (adhesive force) between the layer b and the hydrophilic polymer.

The reactive functional group included in the polymer b is preferably at least one of a hydroxy group, a carboxy group, an amino group, an isocyanate group, or a trialkoxysilyl group.

The reactive functional group is preferably included in at least one of the acrylic acid component, the acrylic acid ester component, the acrylamide component, or the styrene component, which are constituent components of the polymer b.

The number of reactive functional groups in one molecule of the polymer b is not particularly limited as long as the effects of the present invention are not impaired. The number is normally 2 or more, preferably 2 to 300, and more preferably 50 to 300. When the polymer b forms a crosslinked structure described later, a raw material compound for introducing a polysiloxane structure preferably has 2 to 300 reactive functional groups and more preferably 50 to 300 reactive functional groups.

When the polymer b has a polysiloxane structure in its main chain, the average number of repetitions of polysiloxane is preferably 3 to 10000, more preferably 135 to 5000, and further preferably 200 to 1000. The average number of repetitions may be 100 or more or may be 120 or more. The content of the polysiloxane structure in the polymer b is preferably 1 to 70 mass %, more preferably 5 to 60 mass %, and further preferably 10 to 50 mass %.

When the polymer b has a polysiloxane structure in its side chain (graft chain), the average number $n1$ of repetitions in formula (1) below can be preferably applied. In this case, the content of the polysiloxane structure in the polymer b is preferably 1 to 70 mass %, more preferably 5 to 60 mass %, and further preferably 10 to 50 mass %.

The average number of repetitions can be calculated by, for example, NMR measurement or the like.

The content of the polysiloxane structure in the polymer b can be calculated based on the content of Si atoms measured by NMR or the like.

In the insertion auxiliary tube according to an embodiment of the present invention, when the polymer b has a polysiloxane structure, flexibility, and a polar group, both the adhesiveness between the layer b and the tubular substrate a and the adhesiveness between the layer b and a layer c described later can be probably improved. As a result, it is presumed that even if the insertion auxiliary tube is left while being bent with a large curvature, the lubricating layer is less likely to peel off from the tubular substrate a and cracking in the lubricating layer can be suppressed.

The polymer b is preferably a graft polymer having the polysiloxane structure in a graft chain. The graft polymer preferably has a structure that has a structural unit represented by formula (1) below and having a polysiloxane structure in a graft chain and that has at least one of a structural unit represented by formula (2) below as an acrylic acid component or an acrylic acid ester component, a structural unit represented by formula (3) below as an acrylamide component, or a structural unit represented by formula (4) below as a styrene component.

Herein, the "graft polymer having a polysiloxane structure in a graft chain" refers to a polymer having a graft chain having a polysiloxane structure as a side chain bonded to a polymer main chain. That is, the graft chain is a chain that does not include atoms constituting the main chain.

Structural Unit Having Polysiloxane Structure in Graft Chain

Formula (1)

In the formula (1). $R^1$ to $R^6$ represent a hydrogen atom or an organic group.

Examples of the organic group represented by $R^1$ to $R^6$ include an alkyl group, a cycloalkyl group, an alkenyl group, an aryl group, a heteroaryl group, an alkoxy group, an aryloxy group, a heteroaryloxy group, an alkylthio group, an arylthio group, a heteroarylthio group, an alkylamino group, an arylamino group, a heteroarylamino group, an alkyloxycarbonyl group, an aryloxycarbonyl group, a heteroaryloxycarbonyl group, an alkylaminocarbonyl group, an arylaminocarbonyl group, a heteroarylaminocarbonyl group, and a halogen atom. The organic group is preferably an alkyl group, a cycloalkyl group, an alkenyl group, or an aryl group.

The number of carbon atoms of the alkyl group represented by $R^1$ to $R^6$ is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

The number of carbon atoms of the cycloalkyl group represented by $R^1$ to $R^6$ is preferably 3 to 10, more preferably 5 to 10, and further preferably 5 or 6. The cycloalkyl group is preferably a three-membered ring, a five-membered ring, or a six-membered ring and more preferably a five-membered ring or a six-membered ring. Specific examples of the cycloalkyl group represented by $R^1$ to $R^6$ include cyclopropyl, cyclopentyl, and cyclohexyl.

The number of carbon atoms of the alkenyl group represented by $R^1$ to $R^6$ is preferably 2 to 10, more preferably 2 to 4, and further preferably 2. Specific examples of the alkenyl group include vinyl, allyl, and butenyl.

The number of carbon atoms of the aryl group represented by $R^1$ to $R^6$ is preferably 6 to 12, more preferably 6 to 10, and further preferably 6 to 8. Specific examples of the aryl group include phenyl, tolyl, and naphthyl.

The heteroaryl group represented by $R^1$ to $R^6$ is more preferably a five-membered or six-membered heteroaryl group having at least one of an oxygen atom, a sulfur atom, or a nitrogen atom as a ring-constituting atom. The heteroaryl group may be monocyclic or may have a fused ring. Specific examples of the heteroaryl group include 2-pyridyl, 2-thienyl, 2-furanyl, 3-pyridyl, 4-pyridyl, 2-imidazolyl, 2-benzimidazolyl, 2-thiazolyl, 2-benzothiazolyl, and 2-oxazolyl.

The preferred form of the aryl group constituting the aryloxy group, the arylthio group, the arylamino group, the aryloxycarbonyl group, and the arylaminocarbonyl group that are represented by $R^1$ to $R^6$ is the same as the form of the aryl group represented by $R^1$ to $R^6$.

The preferred form of the heteroaryl group constituting the heteroaryloxy group, the heteroarylthio group, the heteroarylamino group, the heteroaryloxycarbonyl group, and the heteroarylaminocarbonyl group that are represented by $R^1$ to $R^6$ is the same as the form of the heteroaryl group represented by $R^1$ to $R^6$.

The preferred form of the alkyl group constituting the alkoxy group, the alkylthio group, the alkylamino group, the alkyloxycarbonyl group, and the alkylaminocarbonyl group that are represented by $R^1$ to $R^6$ is the same as the form of the alkyl group represented by $R^1$ to $R^6$.

Examples of the halogen atom represented by $R^1$ to $R^6$ include a fluorine atom, a chlorine atom, a bromine atom, and an iodine atom. The halogen atom is preferably a fluorine atom or a bromine atom.

When $R^1$ to $R^6$ represent an organic group, the organic group may be unsubstituted or substituted.

$R^1$ to $R^6$ preferably represent an alkyl group, a cycloalkyl group, an alkenyl group, or an aryl group, more preferably represent an alkyl group, an alkenyl group, or an aryl group, and further preferably represent an alkyl group having 1 to 4 carbon atoms. Among them, $R^1$ to $R^5$ preferably represent a methyl group, and $R^6$ preferably represents a butyl group.

In the formula (1), $L^1$ represents a single bond or a divalent linking group.

The divalent linking group represented by $L^1$ is not particularly limited as long as the effects of the present invention are produced. When $L^1$ represents a divalent linking group, the molecular weight of $L^1$ is preferably 10 to 200, more preferably 20 to 100, and further preferably 30 to 70.

When $L^1$ represents a divalent linking group, the divalent linking group is preferably, for example, a divalent linking group obtained by combining two or more divalent groups selected from the group consisting of an alkylene group, an arylene group, —C(=O)—, —O—, and —NR$^L$—. $R^L$ represents a hydrogen atom or a substituent. When $R^L$ represents a substituent, the substituent is preferably an alkyl group. The number of carbon atoms of the alkyl group is preferably 1 to 6 and more preferably 1 to 4, and methyl or ethyl is further preferred.

The alkylene group that may constitute $L^1$ may be linear or branched. The number of carbon atoms of the alkylene group is preferably 1 to 10, more preferably 1 to 6, and further preferably 1 to 3.

The arylene group that may constitute $L^1$ preferably has 6 to 20 carbon atoms, more preferably has 6 to 15 carbon atoms, further preferably has 6 to 12 carbon atoms, and particularly preferably a phenylene group.

$L^1$ preferably represents a divalent linking group obtained by combining two or more divalent groups selected from the group consisting of an alkylene group, —C(=O)—, —O—, and —NR$^L$—.

The number of combinations of the divalent groups represented by $L^1$ is not particularly limited as long as the molecular weight of $L^1$ is satisfied, and is preferably, for example, 2 to 10.

In the formula (1), n1 represents an average number of repetitions, which is 3 to 10,000. When the structural unit of the formula (1) includes a certain amount of repeating siloxane bonds, the adhesiveness between the tubular substrate a and the layer b can be sufficiently improved even if the surface free energy of the surface of the tubular substrate a on which the layer b is to be formed is low. From this viewpoint, n1 is preferably 135 to 10,000, more preferably 150 to 5000, and further preferably 200 to 1000.

The average number of repetitions can be calculated by, for example, NMR measurement.

In the polymer b, the content of the structural unit represented by the formula (1) is preferably 1 to 70 mass %, more preferably 5 to 60 mass %, and further preferably 10 to 50 mass %.

The structural unit represented by the formula (1) can be introduced to the polymer b by using a macromonomer having a particular structure as a raw material. The macromonomer can be synthesized by a typical method, and a commercially available product can also be used. Examples of the commercially available product include X-22-174ASX, X-22-174BX, KF-2012, X-22-2426, and X-22-2404 (trade name, each manufactured by Shin-Etsu Chemical Co., Ltd.), AK-5, AK-30, and AK-32 (trade name, each manufactured by Toagosei Co., Ltd.), and MCR-M07, MCR-M11, MCR-M17, and MCR-M22 (trade name, each manufactured by Gelest, Inc.).

Acrylic Acid Component or Acrylic Acid Ester Component

Formula (2)

In the formula (2), $R^7$ and $R^a$ represent a hydrogen atom or an organic group.

The form of the organic group represented by $R^7$ may be the form of the organic group represented by $R^1$ in the above formula (1). Among them, $R^1$ preferably represents a hydrogen atom or an alkyl group. The number of carbon atoms of the alkyl group is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

The form of the organic group represented by $R^a$ may be the form of the organic group represented by $R^1$ in the above formula (1). Among them, $R^a$ preferably represents a hydrogen atom, an alkyl group, or an aryl group. The alkyl group represented by $R^a$ preferably has 1 to 10 carbon atoms and more preferably has 1 to 6 carbon atoms. Specific examples of the alkyl group include methyl, ethyl, n-propyl, isopropyl, n-butyl, isobutyl, n-hexyl, n-octyl, 2-ethylhexyl, and n-decyl.

The aryl group represented by $R^a$ preferably has 6 to 12 carbon atoms, more preferably has 6 to 10 carbon atoms, further preferably has 6 to 8 carbon atoms, and particularly preferably has 6 carbon atoms. Specific examples of the aryl group include phenyl, tolyl, and naphthyl.

When $R^7$ and $R^a$ represent an organic group, the organic group may be unsubstituted or substituted. When the polymer b has the structural unit represented by the formula (2), at least a part of the structural units represented by the formula (2) in the polymer b preferably has the above-described reactive functional group as a substituent.

In the structural unit represented by the formula (2) that may be present in the polymer b, when $R^a$ represents an alkyl group having a substituent, $R^a$ also preferably represents a group represented by formula (5) below in at least a part of the structural units.

Formula (5)

In the formula (5), n2 represents an average number of repetitions, which is an integer of 1 to 10,000. Herein, n2 preferably represents 1 to 8000, more preferably represents 1 to 5000, and further preferably represents 1 to 3000.

The average number of repetitions can be calculated by, for example, NMR measurement.

$R^{10}$ represents a hydrogen atom or an organic group. The form of the organic group represented by $R^{10}$ may be the form of the organic group represented by $R^1$ in the above formula (1). When $R^{10}$ represents an organic group, the organic group may be unsubstituted or substituted. $R^{10}$ preferably represents a hydrogen atom or an alkyl group. Specific examples of the alkyl group include methyl, ethyl, n-propyl, isopropyl, n-butyl, isobutyl, n-hexyl, n-octyl, 2-ethylhexyl, and n-decyl.

* represents a bonding site to an oxygen atom (—O—) in the formula (2).

$R^a$ also preferably represents a nitrogen-containing organic group in at least a part of the structural units represented by the formula (2) that may be present in the polymer b. The molecular weight of the nitrogen-containing organic group is preferably 10 to 200 and more preferably 20 to 100. The nitrogen-containing organic group is preferably an amino group (including a substituted amino group in addition to an unsubstituted amino group). Preferred examples of the nitrogen-containing organic group include an alkylamino group, an alkylaminoalkyl group, an arylamino group, an arylaminoalkyl group, a heteroarylamino group, and a heteroarylaminoalkyl group.

When $R^a$ represents the group represented by the formula (5) or the nitrogen-containing organic group, it is believed that the interaction between the polymer including a polysiloxane structure and a crosslinking agent component is strengthened.

Acrylamide Component

Formula (3)

In the formula (3), $R^8$, $R^{b1}$, and $R^{b2}$ represent a hydrogen atom or an organic group.

The form of the organic group represented by $R^8$ may be the form of the organic group represented by $R^1$ in the above formula (1). $R^8$ preferably represents a hydrogen atom or an alkyl group and more preferably represents an alkyl group. The number of carbon atoms of the alkyl group is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

The organic group represented by $R^{b1}$ and $R^{b2}$ is, for example, the organic group represented by $R^1$ in the above formula (1). In particular, $R^{b1}$ and $R^{b2}$ preferably represent a hydrogen atom, an alkyl group, or an aryl group. The number of carbon atoms of the aryl group is preferably 6 to 12, more preferably 6 to 10, further preferably 6 to 8, and particularly preferably 6. Specific examples of the aryl group include phenyl, tolyl, and naphthyl.

When $R^8$, $R^{b1}$, and $R^{b2}$ represent an organic group, the organic group may be unsubstituted or substituted. When the polymer b has the structural unit represented by the formula (3), at least a part of the structural units represented by the formula (3) in the polymer b preferably has the above-described reactive functional group as a substituent.

Styrene Component

Formula (4)

In the formula (4), $R^9$ represents a hydrogen atom or an organic group. $R^{c1}$ to $R^{c5}$ represent a hydrogen atom, a halogen atom, or an organic group.

The form of the organic group represented by $R^9$ may be the form of the organic group represented by $R^1$ in the above formula (1). In particular, $R^9$ preferably represents a hydrogen atom.

The form of the organic group represented by $R^{c1}$ to $R^{c5}$ may be the form of the organic group represented by $R^1$ in the above formula (1). The halogen atom represented by $R^{c1}$ to $R^{c5}$ is not particularly limited. The halogen atom is preferably a fluorine atom or a bromine atom and more preferably a fluorine atom. $R^{c1}$ to $R^{c5}$ preferably represent a hydrogen atom, an alkyl group, or a halogen atom. The number of carbon atoms of the alkyl group is preferably 1 to 10, more preferably 1 to 4, further preferably 1 or 2, and particularly preferably 1. Specific examples of the alkyl group include methyl, ethyl, n-propyl, isopropyl, n-butyl, isobutyl, n-hexyl, n-octyl, 2-ethylhexyl, and n-decyl.

When $R^9$ and $R^{c1}$ to $R^{c5}$ represent an organic group, the organic group may be unsubstituted or substituted. When the polymer b has the structural unit represented by the formula (4), at least a part of the structural units represented by the formula (4) in the polymer b preferably has the above-described reactive functional group as a substituent.

When the polymer b has a structural unit represented by any of the formulae (2) to (4), the total amount of the structural unit in the polymer b is preferably 10 to 90 mass %, more preferably 15 to 80 mass %, and further preferably 20 to 70 mass %.

When the polymer b has a structural unit that is represented by any of the formulae (2) to (4) and that has the above-described reactive functional group, the content of the structural unit in the polymer b is preferably 5 to 70 mass %, more preferably 10 to 50 mass %, further preferably 10 to 30 mass %, and particularly preferably 15 to 30 mass %.

The polymer b may have another structural unit in addition to the structural unit represented by the formula (1), the structural unit represented by any of the formulae (2) to (4), and a crosslinking agent component described later as long as the effects of the present invention are produced.

The polymer b can be synthesized by a typical method. For example, the polymer b is obtained by reacting a monomer that results in a desired structural unit and a polymerization initiator by a typical method. The polymerization reaction may be any of anionic polymerization, cationic polymerization, and radical polymerization, but radical polymerization is preferred. The polymer obtained by the polymerization reaction is also preferably subjected to purification by a reprecipitation method or the like.

When the composition according to an embodiment of the present invention is prepared, the polymer b may be provided in the form of either solution or solid.

Any polymerization initiator can be used in accordance with the form of the polymerization reaction (anionic polymerization, cationic polymerization, or radical polymerization) The polymerization initiator may be either a thermal polymerization initiator or a photopolymerization initiator. The molecular weight of the polymerization initiator is not limited, and any polymerization initiator having a low molecular weight to a high molecular weight may be used.

Specific examples of the radical polymerization initiator include organic peroxides and azo compounds.

Other examples include high-molecular-weight polymerization initiators having a peroxide structure or an azo structure in the polymer chain (preferably in the main chain), such as a peroxide high-molecular-weight polymerization initiator and an azo high-molecular-weight polymerization initiator.

The high-molecular-weight polymerization initiator also preferably has the above-described polysiloxane structure. The high-molecular-weight polymerization initiator having a polysiloxane structure functions as a polymerization initiator and also serves as the above-described constituent component having a polysiloxane structure. Thus, the polymer b can be obtained.

The number of peroxide structures or azo structures in the high-molecular-weight polymerization initiator is not particularly limited, but is preferably 2 or more. The weight-average molecular weight of the high-molecular-weight polymerization initiator is also not particularly limited.

Any commercially available high-molecular-weight polymerization initiator can be used. The polymerization initiator is, for example, a polydimethylsiloxane unit-containing high-molecular-weight azo polymerization initiator VPS-1001N (trade name, manufactured by Wako Pure Chemical Industries, Ltd.).

The polymer b also preferably has a crosslinked structure formed using a crosslinking agent. In this case, the crosslinking agent preferably includes at least one of a crosslinking agent (polymeric crosslinking agent) having a structural unit represented by formula (6) below or a crosslinking agent represented by formula (7) below. By forming a crosslinked structure using these crosslinking agents, the layer b can be cured to further increase the mechanical strength. These crosslinking agents normally interact or react with the reactive functional group of each structural unit described above to form a crosslinked structure in the polymer b. The crosslinking reaction can be caused by a typical method in accordance with the type of group contributing to the crosslinking reaction.

Formula (6)

Formula (7)

In the formula (6), $R^{11}$ represents a hydrogen atom or an organic group. When $R^{11}$ represents an organic group, the organic group may have a substituent. $R^{11}$ preferably represents a hydrogen atom or an alkyl group (preferably an alkyl group having 1 to 5 carbon atoms, more preferably an alkyl group having 1 to 3 carbon atoms). X represents a hydroxy group, a carboxy group, an amino group, an isocyanate group, an oxazolinyl group, an epoxy group, a vinyl group, an ethynyl group, a sulfanyl group, an azide group, a trialkoxysilyl group, or a group having an acid anhydride structure. X may have a substituent.

The crosslinking agent represented by the formula (6) is, for example, an oxazolinyl group-containing polymer (trade name: EPOCROS (registered trademark), manufactured by Nippon Shokubai Co., Ltd.). The oxazolinyl group-containing polymer is, for example, a polymer constituted by the following structural units. In this specification, Me represents methyl.

When the crosslinking agent is a polymer and includes an acrylic acid component, an acrylic acid ester component, an acrylamide component, or a styrene component as a constituent component, these components are respectively included in the acrylic acid component, the acrylic acid ester component, the acrylamide component, and the styrene component defined in the present invention.

In the formula (7), Y represents an m-valent linking group. Y preferably represents a hydrocarbon group in which the number of carbon atoms is an integer of 2 to 20 or the number of carbon atoms is an integer of 2 to 15. The hydrocarbon group may have a heteroatom in its hydrocarbon chain. Examples of the hetero atom include O, S, N, and Ti. Furthermore, m represents an integer of 2 or more, preferably represents 2 to 8, and more preferably represents 2 to 4. $R^{dm}$ has the same definition as X in the formula (6).

Examples of the crosslinking agent represented by the formula (7) include polyisocyanate compounds (preferably diisocyanate compounds) silane coupling agents, and titanium coupling agents. Examples of the crosslinking agent represented by the formula (7) are shown below.

When the polymer b has a crosslinked structure formed using a crosslinking agent, the content of the crosslinking agent component (crosslinking agent-derived component) in the polymer b having a crosslinked structure is preferably 30 to 90 mass % and more preferably 40 to 70 mass %. The content may be 20 to 60 mass %.

The weight-average molecular weight of the polymer b (in a case where the polymer b has a crosslinked structure formed using a crosslinking agent, the weight-average molecular weight of the polymer b before crosslinking) is preferably 10,000 to 300,000, more preferably 30,000 to 150,000, and further preferably 40,000 to 120,000.

The layer b may include a single polymer b or two or more polymers b. The content of the polymer b in the layer b is preferably 5 mass % or more, more preferably 10 mass % or more, and further preferably 20 mass % or more. The content of the polymer b in the layer b is also preferably 40 mass % or more, more preferably 60 mass % or more, and further preferably 80 mass % or more. When the layer b includes a component other than the polymer b, examples of the component other than the polymer b include a polymer binder, a surfactant, polymer fine particles, and inorganic fine particles.

The surface of the layer b is preferably subjected to hydrophilic treatment. As a result of the hydrophilic treatment, a silicone chain is partly hydrolyzed to form a low-molecular-weight silicone chain. This silicone chain improves the flexibility of the layer b, which improves adhesiveness and crack resistance. In the present invention, the "surface of the layer b" means a surface opposite to a surface of the layer b in contact with the tubular substrate a.

The method of hydrophilic treatment is not particularly limited as long as a hydrophilic group can be provided to the surface of the layer b (a polymer b present on the surface of the layer b). For example, the surface of the layer b can be hydrophilized by immersion in an acidic solution, immersion in an alkaline solution, immersion in a peroxide solution, plasma treatment, or electron beam irradiation. The insertion auxiliary tube according to an embodiment of the present invention produces a desired effect even if the layer b is not subjected to surface treatment including hydrophilic treatment.

The thickness of the layer b is normally 0.01 to 100 μm, preferably 0.05 to 50 μm, and more preferably 0.1 to 10 μm.

Insertion Auxiliary Tube with Hydrophilic Coating Layer

Figure 2:
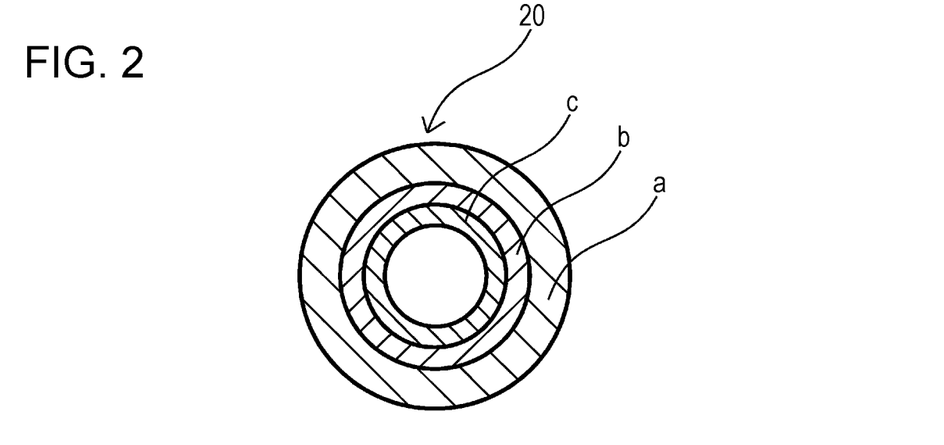
FIG. 2 is a sectional view illustrating an insertion auxiliary tube with a hydrophilic coating layer according to an embodiment of the present invention.

The insertion auxiliary tube with a hydrophilic coating layer according to an embodiment of the present invention is provided by forming a layer c including a hydrophilic polymer on the surface of the layer b constituting the insertion auxiliary tube according to an embodiment of the present invention. That is, as illustrated in FIG. 2 (FIG. 2 illustrates one embodiment in which an insertion auxiliary tube with a hydrophilic coating layer is produced using the insertion auxiliary tube in FIG. 1), the insertion auxiliary tube with a hydrophilic coating layer according to an embodiment of the present invention has the insertion auxiliary tube according to an embodiment of the present invention and a layer c including a hydrophilic polymer and disposed on the layer b (the surface of the layer b) constituting the insertion auxiliary tube. Examples of the hydrophilic polymer include polyvinylpyrrolidone, a vinyl ether-maleic anhydride copolymer, polyethylene glycol, polyacrylic acid, polyacrylamide, and hyaluronic acid. One or more of the hydrophilic polymers can be used. The hydrophilic polymer is preferably at least one of polyvinylpyrrolidone, vinyl ether-maleic anhydride, or polyethylene glycol.

The content of the hydrophilic polymer in the layer c is preferably 50 mass % or more, more preferably 70 mass % or more, further preferably 80 mass % or more, and particularly preferably 90 mass % or more. When the layer c includes a component other than the hydrophilic polymer, examples of the component other than the hydrophilic polymer include a polymer binder, a surfactant, polymer fine particles, inorganic fine particles, and a crosslinking agent.

The layer c can be formed by preparing a solution (a coating solution for forming a layer c) in which a hydrophilic polymer is dissolved, applying this solution onto the layer b, and drying the solution. The solution may contain a crosslinking agent in accordance with the purpose. Examples of the solvent used for the coating solution for forming a layer c include ether solvents such as dibutyl ether, dimethoxymethane, dimethoxyethane, diethoxyethane, propylene oxide, 1,4-dioxane, 1,3-dioxolane, 1,3,5-trioxane, tetrahydrofuran, anisole, and phenetole; ketone solvents such as acetone, methyl ethyl ketone, diethyl ketone, dipropyl ketone, diisobutyl ketone, methyl isobutyl ketone, cyclopentanone, cyclohexanone, methylcyclohexanone, and dimethylcyclohexanone; ester solvents such as ethyl formate, propyl formate, n-pentyl formate, methyl acetate, ethyl acetate, methyl propionate, ethyl propionate, n-pentyl acetate, and γ-butyrolactone; alcohol solvents such as methanol, ethanol, 1-propanol, 2-propanol, 1-butanol, 2-butanol, tert-butanol, 1-pentanol, 2-methyl-2-butanol, and cyclohexanol; aromatic hydrocarbons such as xylene and toluene; halogenated hydrocarbon solvents such as methylene chloride, chloroform, and 1,1-dichloroethane; amide solvents such as N-methyl-2-pyrrolidone (NMP), N,N-dimethylformamide (DMF), and N,N-dimethylacetamide (DMAc); nitrile solvents such as acetonitrile; and organic solvents having two or more functional groups, such as methyl 2-methoxyacetate, methyl 2-ethoxyacetate, ethyl 2-ethoxyacetate, ethyl 2-ethoxypropionate, 2-methoxyethanol, 2-propoxyethanol, 2-butoxyethanol, 1,2-diacetoxyacetone, acetylacetone, diacetone alcohol, methyl acetoacetate, N-methylpyrrolidone, propylene glycol monomethyl ether acetate, and ethyl acetoacetate.

The layer c may have a crosslinked structure. Examples of the crosslinking agent included in the coating solution for forming a layer c include a polyisocyanate compound (preferably a diisocyanate compound), a silane coupling agent, a titanium coupling agent, a polyepoxy compound, a polyamine compound, and a melamine compound.

The thickness of the layer c is preferably 0.1 to 100 μm, more preferably 0.5 to 50 μm, and further preferably 1 to 10 μm.

The insertion auxiliary tube according to an embodiment of the present invention is preferably provided with an inflatable and deflatable balloon on the outer surface of the distal end thereof. For example, by holding the insertion auxiliary tube in a body cavity through inflation of the balloon, the insertion of the endoscope into the body cavity can be assisted and facilitated. For example, JP2005-278846A can be referred to as a specific example of an overtube provided with an inflatable and deflatable balloon and as a usage example of the overtube.

The outer diameter (φ) of the insertion auxiliary tube according to an embodiment of the present invention can be appropriately adjusted in accordance with the application. When the insertion auxiliary tube is used as an insertion auxiliary tube of an endoscope (endoscope overtube) and the outer diameter of the endoscope inserted into the insertion auxiliary tube is 4 to 13 mm, the outer diameter (φ) is preferably 7 to 20 mm and more preferably 10 to 14 mm. The outer diameter (φ) refers to the maximum outer diameter when the shape of the longitudinal section of the endoscope overtube is not a perfect circle.

Set of Insertion Auxiliary Tube and Endoscope According to Embodiment of the Present Invention The insertion auxiliary tube according to an embodiment of the present invention is preferably used as an insertion auxiliary tube of an endoscope. That is, the insertion auxiliary tube can be combined with an endoscope and distributed as a set of the insertion auxiliary tube and the endoscope for use. In this set, before use the endoscope and the insertion auxiliary tube may be separated from each other or an insertion part of the endoscope may be inserted into the insertion auxiliary tube.

In the above set, when the insertion auxiliary tube has a smaller length than the insertion part of the endoscope, the difference in length between the insertion part and the insertion auxiliary tube (the length of the insertion part of the endoscope−the length of the insertion auxiliary tube) is not particularly limited. From the viewpoint of repeatedly performing a forward movement of the endoscope relative to the insertion auxiliary tube and then a forward movement of the insertion auxiliary tube, the difference is preferably 200 to 800 mm and more preferably 400 to 600 mm.

Endoscope Apparatus According to Embodiment of the Present Invention

An endoscope apparatus according to an embodiment of the present invention includes the insertion auxiliary tube (endoscope insertion auxiliary tube) according to an embodiment of the present invention and an endoscope. In the endoscope apparatus, for example, by rotating the endoscope insertion auxiliary tube according to an embodiment of the present invention, the endoscope insertion auxiliary tube and the endoscope are allowed to reach a deep position of a living body. Specific examples of the endoscope apparatus according to an embodiment of the present invention include combinations of the insertion auxiliary tube according to an embodiment of the present invention and apparatuses described in JP5519888B, JP2014-64686A, WO2016/00971 IA, WO2015/198946A, WO2015/125376A, and WO2015/118773A. In addition to the endoscope insertion auxiliary tube and the endoscope, the endoscope apparatus according to an embodiment of the present invention further includes, for example, a light source unit, a processor that performs video processing, and a pump unit that sends air to a balloon of an overtube.

Hereafter, the specific examples will be further described in detail, but the endoscope apparatus according to an embodiment of the present invention is not limited to the following description.

(1) An endoscope apparatus in which the endoscope auxiliary tube according to an embodiment of the present invention is used as a rotation unit 30 in the endoscope apparatus illustrated in FIG. 1 of JP5519888B (2) An endoscope apparatus in which a tube obtained by disposing a spiral fin portion on an outer peripheral surface of the endoscope auxiliary tube according to an embodiment of the present invention is used as a spiral tube in the endoscope apparatus including a device for introduction into a living body or including a device for introduction into a living body at an insertion part in JP2014-64686A (3) An endoscope apparatus in which the endoscope auxiliary tube according to an embodiment of the present invention is used as a rotary cylindrical body in the insertion apparatus described in WO2016/009711A (4) An endoscope apparatus in which the endoscope auxiliary tube according to an embodiment of the present invention is used as an attachment unit 132 in the device for introduction into a living body illustrated in FIG. 1 of WO2015/198946

(5) An endoscope apparatus in which the endoscope auxiliary tube according to an embodiment of the present invention is used as an attachment unit 132 in the device for introduction into a living body illustrated in FIG. 1 of WO2015/125376A (6) An endoscope apparatus in which the endoscope auxiliary tube according to an embodiment of the present invention is used as a tube main body 31 in the endoscope apparatus illustrated in FIG. 1 of WO2015/118773

The endoscope insertion auxiliary tube according to an embodiment of the present invention may be automatically rotated. Alternatively, the endoscope insertion auxiliary tube may be allowed to reach a deep position of a body cavity together with the endoscope by performing manual rotation.

In the endoscope apparatus according to an embodiment of the present invention, the difference in length between the insertion part of the endoscope and the insertion auxiliary tube (the length of the insertion part of the endoscope−the length of the insertion auxiliary tube) is preferably in the same range as that described in the above "set".

Method for Producing Insertion Auxiliary Tube According to Embodiment of the Present Invention The method for producing an insertion auxiliary tube according to an embodiment of the present invention is a method for producing an insertion auxiliary tube having a tubular substrate a and a layer b disposed on the tubular substrate a. The step of forming the layer b includes applying a composition (the composition according to an embodiment of the present invention) including a polymer including a polysiloxane structure onto the tubular substrate a.

The method of applying the composition is not particularly limited. Examples of the method include a method in which the tubular substrate a is immersed in the composition, a method in which the composition is injected into the tubular substrate a for immersion, and a method in which the composition is caused to flow through inside the tubular substrate a.

The method for producing an insertion auxiliary tube according to an embodiment of the present invention may include a step of performing heating for drying, a crosslinking reaction, or the like. The number of heating steps may be one or more. The heating conditions are, for example, 40° C. to 170° C. and 10 to 120 minutes.

The method for producing an insertion auxiliary tube according to an embodiment of the present invention may include hydrophilic treatment. The hydrophilic treatment can be performed by, for example, immersing the layer b in or contacting the layer b with a 10% aqueous hydrochloric acid solution, a 5% aqueous sodium hydroxide solution, acetic acid, or a hydrogen peroxide solution for 30 to 640 minutes, then washing the layer b with methanol, ethanol, propanol, or isopropanol, and drying the layer b at 40° C. to 100° C. for 10 to 90 minutes.

EXAMPLES

Hereafter, the present invention will be further described in detail based on Examples. The present invention should not be construed as being limited to Examples.

1. Preparation of Polymer and Polymer Solution

Synthesis Example 1 (Synthesis of Polymer 1)

Seventy grams of a polydimethylsiloxane unit-containing high-molecular-weight azo polymerization initiator VPS-1001N (trade name, manufactured by Wako Pure Chemical Industries, Ltd., weight-average molecular weight of polysiloxane unit: 10,000) and 30 g of 2-hydroxyethyl methacrylate were mixed and stirred at 75° C. for 4 hours in a nitrogen atmosphere to cause a polymerization reaction. The resulting reaction solution was added to 1000 mL of methanol to generate a white solid. The resulting white solid was washed with methanol and dried to obtain a polymer 1. The weight-average molecular weight of the polymer 1 was 35000.

Polymer 1

Synthesis Example 2 (Preparation of Solution of Polymer 2)

To a reaction apparatus equipped with a reflux column and a stirrer, 16.0 g of silicone macromer AK-32 (trade name, manufactured by Toagosei Co., Ltd., number-average molecular weight: 20,000), 4.0 g of hydroxyethyl methacrylate (manufactured by Tokyo Chemical Industry Co., Ltd.), 10.0 g of methoxy polyethylene glycol methacrylate (hereafter referred to as MPEGA) (manufactured by Aldrich, number-average molecular weight: 5,000), 10.0 g of methyl methacrylate (manufactured by Tokyo Chemical Industry Co., Ltd.), 0.03 g of azobisisobutyronitrile (AIBN) (manufactured by Wako Pure Chemical Industries, Ltd.), and 60 g of methyl ethyl ketone (MEK) (manufactured by Wako Pure Chemical Industries, Ltd.) were added, and stirring was performed at 80° C. for 20 hours to cause a polymerization reaction. The obtained reaction solution was used as a solution of the polymer 2. The weight-average molecular weight of the polymer 2 was 20,000.

Polymer 2

Synthesis Example 3 (Synthesis of Polymer 3)

Seventy grams of a polydimethylsiloxane unit-containing high-molecular-weight azo polymerization initiator VPS-1001N (trade name, manufactured by Wako Pure Chemical Industries, Ltd., weight-average molecular weight of polysiloxane unit: 10,000) and 30 g of methacrylic acid were mixed and stirred at 75° C. for 4 hours in a nitrogen atmosphere to cause a polymerization reaction. The resulting reaction solution was added to 1000 mL of methanol to generate a white solid. The resulting white solid was washed with methanol and dried to obtain a polymer 3. The weight-average molecular weight of the polymer 3 was 35000.

Polymer 3

2. Preparation of Coating Solution for Forming Layer b

Components selected from the group consisting of a polymer, a polymer solution, and a crosslinking agent were dissolved in a solvent in amounts shown in Table 1 below to prepare coating solutions 1 to 5 for forming a layer b. In Table 1, the amount is expressed in units of parts by mass, and "-" means that the corresponding component is not contained.

TABLE 1

|  |  | Coating solution 1 | Coating solution 2 | Coating solution 3 | Coating solution 4 | Coating solution 5 | Coating solution 6 |
|---|---|---|---|---|---|---|---|
| Polymer | Polymer 1 | 5 | — | 2.5 | — | — | — |
|  | Polymer 2 (solution) | — | 12.5 | — | — | — | 6.25 |
|  | Polymer 3 | — | — | — | 2.5 | — | — |
|  | Lubricating material in JP2004-524903A (polytetrafluoroethylene gel) | — | — | — | — | 5 | — |
| Crosslinking agent | EPOCROS WS-500 | — | — | 2.5 | 2.5 | — | 2.5 |
| Solvent | Isopropyl alcohol | 95 | 87.5 | 95 | 95 | 95 | 91.25 |
| Total |  | 100 | 100 | 100 | 100 | 100 | 100 |

Note in Table
Polymer 2: the solution of the polymer 2 prepared above and having a solid content of 40 mass %
EPOCROS WS-500 (trade name): oxazolinyl group-containing polymer, manufactured by Nippon Shokubai Co., Ltd., oxazolinyl group content 4.5 mmol/g, solid content 40 mass %

3. Preparation of Hydrophilic Coating Solution

A hydrophilic coating solution was prepared by dissolving 2.0 g of polyvinylpyrrolidone (K-90 (trade name), manufactured by Wako Pure Chemical Industries, Ltd.) and 0.25 g of 4,4 diphenylmethane diisocyanate (MDI) (manufactured by Tokyo Chemical Industry Co., Ltd.) in 100 g of chloroform.

4. Production of Insertion Auxiliary Tube

Example 1

An insertion auxiliary tube in Example 1 was produced as follows.

Figure 3:
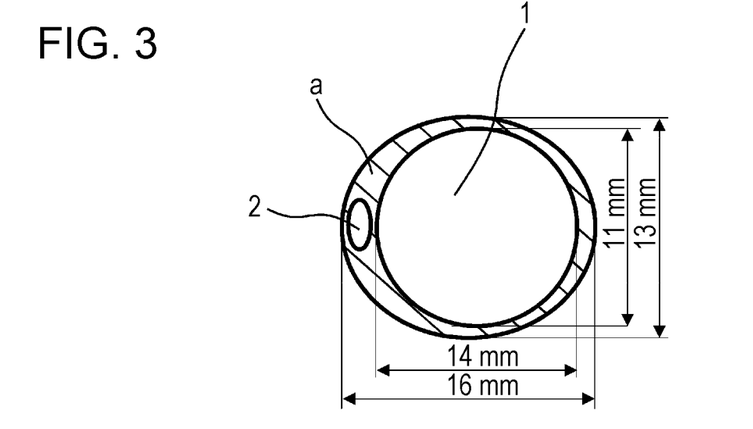
FIG. 3 is a longitudinal sectional view of a tubular substrate a used in Examples.

A urethane resin tube (length 1500 mm, Shore A hardness 80) having the dimensions of a longitudinal section in FIG. 3 was used as a tubular substrate a. The inner surface of the tubular substrate a was fixed in a U-shape so that both ends of the tubular substrate a were at the same level. The coating solution 1 was poured from one opening of an insertion hole 1 of the tubular substrate a. After the liquid level reached both the ends, the tubular substrate a was left to stand at room temperature for 3 minutes. After draining the solution from one of the openings, drying by heating was performed at 150° C. for 30 minutes to volatilize or evaporate the solvent in the coating solution 1 applied onto the inner surface of the tubular substrate a. Thus, a layer b was formed.

Examples 2, 3, 7, 8, 10, 11, 13, and 14 and Comparative Example 1

Insertion auxiliary tubes in Examples 2, 3, 7, 8, 10, 11, 13, and 14 and Comparative Example 1 were produced in the same manner as in Example 1, except that coating solutions and tubular substrates a shown in Table 2 were employed. The dimensions of the longitudinal sections of the tubular substrates a used in Examples and Comparative Example are as illustrated in FIG. 3.

Example 4

The insertion auxiliary tube with a layer b produced in Example 2 was fixed in a U-shape so that both ends of the insertion auxiliary tube were at the same level. A 10% aqueous hydrochloric acid solution was poured from one opening of the tube. After the liquid level reached both the ends, the insertion auxiliary tube was left to stand at room temperature for 6 hours. After draining the solution from one of the openings of the insertion hole 1, the inner surface was washed with about 50 mL of methanol and then dried by heating at 60° C. for 30 minutes to prepare an insertion auxiliary tube in Example 4 in which the surface of the layer b was subjected to hydrophilic treatment.

Examples 5, 9, 15, and 16

Insertion auxiliary tubes in Examples 5, 9, 15, and 16 were produced in the same manner as in Example 4, except that coating solutions and tubular substrates a shown in Table 2 were employed.

5. Production of Insertion Auxiliary Tube with Hydrophilic Lubricating Coating Layer (Layer c)

Example 6

The insertion auxiliary tube with a layer b produced in Example 5 was fixed in a U-shape so that both ends of the insertion auxiliary tube were at the same level. A hydrophilic coating solution was poured from one opening of the insertion hole 1 of the insertion auxiliary tube. After the liquid level reached both the ends, the insertion auxiliary tube was left to stand at room temperature for 20 minutes. After draining the solution from one of the openings, the insertion auxiliary tube was dried at 60° C. for 30 minutes and then at 135° C. for 30 minutes to produce an insertion auxiliary tube with a layer c in Example 6.

Examples 12 and 17

Insertion auxiliary tubes were produced in the same manner as in Example 6, except that coating solutions and tubular substrates a shown in Table 2 were employed.

The thickness of the layer b in each of Examples 1 to 5, 7 to 11, and 13 to 16 and Comparative Example 1 was 0.7 μm and the total thickness of the layer b and the layer c in Examples 6, 12, and 17 was 4.0 μm.

The outer diameter of the insertion auxiliary tube in Examples 1 to 17 and Comparative Example 1 was 16 mm.

Test

The insertion auxiliary tube produced above was wound so as to overlap a cylinder having a diameter φ=95 mm and fixed to the cylinder at room temperature for 1 hour (greatly bent). The following test was performed on the greatly bent insertion auxiliary tube. Table 2 collectively shows the test results.

[Test Example 1-1] Crack Resistance Test

A central portion with a length of 70 mm of the insertion auxiliary tube was cut out. The cut tube was cut open to obtain a sheet-like test piece. The number of cracks in the layer b or c of the test piece was visually counted, and evaluation was made based on the following evaluation criteria. In this test, 3 or higher is acceptable.

([the number of squares left/100]×100(%)) was calculated, and evaluation was made based on the following evaluation criteria. In this test, 3 or higher is acceptable.

Evaluation Criteria of Adhesiveness Test
8: 95% or more and 100% or less
7: 90% or more and less than 95%
6: 85% or more and less than 90%
5: 80% or more and less than 85%
4: 60% or more and less than 80%
3: 40% or more and less than 60%
2: 20% or more and less than 40%
1: less than 20%

TABLE 2

| | | | | Layer b | | | | Evaluation | |
| | Tubular substrate a | Shore A hardness*[1] | Coating solution | Crosslinking agent | Content of crosslinking agent component in crosslinked body [mass %]*[2] | Hydrophilic treatment | Layer c | Shore A hardness*[3] | Adhesiveness | Crack resistance |
|---|---|---|---|---|---|---|---|---|---|---|
| Example 1 | Urethane resin | 80 | 1 | — | — | — | — | 80 | 3 | 3 |
| Example 2 | Urethane resin | 80 | 2 | — | — | — | — | 80 | 4 | 3 |
| Example 3 | Urethane resin | 80 | 6 | EPOCROS | 50 | — | — | 80 | 6 | 5 |
| Example 4 | Urethane resin | 80 | 2 | — | — | 10% HCL, 6 h | — | 80 | 6 | 5 |
| Example 5 | Urethane resin | 80 | 6 | EPOCROS | 50 | 10% HCL, 6 h | — | 80 | 7 | 5 |
| Example 6 | Urethane resin | 80 | 6 | EPOCROS | 50 | 10% HCL, 6 h | Formed | 80 | 7 | 6 |
| Example 7 | Urethane resin | 80 | 3 | EPOCROS | 50 | — | — | 80 | 5 | 4 |
| Example 8 | Urethane resin | 80 | 4 | EPOCROS | 50 | — | — | 80 | 5 | 4 |
| Example 9 | Urethane resin | 80 | 1 | — | — | 10% HCL, 6 h | — | 80 | 5 | 4 |
| Example 10 | Silicone resin | 80 | 1 | — | — | — | — | 80 | 5 | 4 |
| Example 11 | Silicone resin | 30 | 1 | — | — | — | — | 30 | 3 | 3 |
| Example 12 | Silicone resin | 80 | 3 | EPOCROS | 50 | 10% HCL, 6 h | Formed | 80 | 6 | 6 |
| Example 13 | Silicone resin | 80 | 2 | — | — | — | — | 80 | 6 | 4 |
| Example 14 | Silicone resin | 80 | 6 | EPOCROS | 50 | — | — | 80 | 7 | 5 |
| Example 15 | Silicone resin | 80 | 2 | — | — | 10% HCL, 6 h | — | 80 | 7 | 5 |
| Example 16 | Silicone resin | 80 | 6 | EPOCROS | 50 | 10% HCL, 6 h | — | 80 | 8 | 5 |
| Example 17 | Silicone resin | 80 | 6 | EPOCROS | 50 | 10% HCL, 6 h | Formed | 80 | 8 | 6 |
| Comparative Example 1 | Urethane resin | 80 | 5 | — | — | — | — | 80 | 2 | 2 |

Note in Table
*[1]indicating the Shore A hardness of the tubular substrate a
*[2]calculated from {mass of crosslinking agent/(mass of polymer + mass of crosslinking agent in Table 1)} × 100 (%)
*[3]indicating the Shore A hardness of the insertion auxiliary tube Evaluation Criteria of Crack Resistance Test
6: 0
5: 1 or 2
4: 3 to 5
3: 6 to 10
2: 11 to 15
1: 16 or more

[Test Example 1-2] Adhesiveness Test

The adhesiveness was evaluated by a tape peel test (conforming to ISO 2409).

The layer b or the layers b and c formed on the surface of the test piece were cut using a cross-cutter to provide 100 squares (10×10) (a grid pattern was formed). The dimensions of each square were 2 mm in length and 2 mm in width. The depth of the cut was 1 μm in Examples 1 to 5, 7 to 11, and 13 to 16 and Comparative Example 1, and 5 μm in Examples 6, 12, and 17. A cellophane (registered trademark) tape (manufactured by Nichiban Co., Ltd., 24 mm in length×40 mm in width) was attached to the test piece so as to cover all of the 25 squares. The percentage of the number of squares at which the layer b or the layers b and c were left on the substrate when the cellophane tape was peeled off Method for Measuring Shore a Hardness The Shore A hardness was measured in conformity with JIS 6253-3.

A test piece with a length of 1 cm was cut out from the tubular substrate a. The test piece was cut open to obtain a sheet-like test piece. The Shore A hardness was measured using a Type A durometer (GS-719N) (trade name, manufactured by Teclock Co., Ltd.) as a test machine.

For the insertion auxiliary tube, the Shore A hardness was measured on the surface on which the layer b or the layers b and c were formed in the same manner as for the tubular substrate a.

As shown in Table 2, in Comparative Example 1, the coating solution for forming a layer b includes a polytetrafluoroethylene gel. The insertion auxiliary tube formed by using this coating solution was unacceptable in terms of adhesiveness and crack resistance.

In contrast, in Examples 1 to 17 satisfying the requirements of the present invention, both adhesiveness and crack resistance were excellent. In Examples 3, 7, 8, and 14, the mechanical strength of the layer b was increased by crosslinking the polymer including a polysiloxane structure with a crosslinking agent. Thus, the adhesiveness and the crack resistance were further improved. In Examples 4, 9, and 15, by subjecting the layer b to hydrophilic treatment, the silicone chain was partly hydrolyzed and the resulting low-molecular-weight silicone chain improved the flexibility of the layer b. Thus, the adhesiveness and the crack resistance were improved. In Examples 5, 6, 12, 16, and 17, the adhesiveness and the crack resistance were improved by both of the above effects.

While the present invention has been described with reference to the embodiments thereof, we do not intend to limit our invention in any detail of the description unless otherwise specified. Rather, the invention should be broadly construed without departing from the spirit and scope of the invention as defined by the appended claims.

REFERENCE SIGNS LIST 10 insertion auxiliary tube
20 insertion auxiliary tube with hydrophilic coating layer
a tubular substrate
b layer including polymer having polysiloxane structure
c layer including hydrophilic polymer
1 insertion hole
2 air hole

What is claimed is:

1. A combination of an insertion auxiliary tube and an endoscope, wherein the insertion auxiliary tube comprises:
a tubular substrate a; and
a layer b disposed on at least one of an inside or an outside of the tubular substrate a,
wherein the layer b includes a polymer
that includes at least one of an acrylic acid component, an acrylic acid ester component, an acrylamide component, or a styrene component as a constituent component, and has at least one of a hydroxy group, a carboxy group, an amino group, an isocyanate group, an oxazolinyl group, an epoxy group, a sulfanyl group, an azide group, a trialkoxysilyl group, or an acid anhydride structure in a molecule thereof,
wherein the polymer includes a structural unit represented by formula (1) below and includes at least one of a structural unit represented by formula (2) below a structural unit represented by formula (3) below, or a structural unit represented by formula (4) below, Formula (1)

wherein $R^1$ to $R^6$ represent a hydrogen atom or an organic group, $L^1$ represents a single bond or a divalent linking group, and n1 represents 3 to 10,000, Formula (2)

wherein $R^7$ and $R^a$ represent a hydrogen atom or an organic group,

Formula (3)

wherein $R^8$, $R^{b1}$, and $R^{b2}$ represent a hydrogen atom or an organic group, and

Formula (4)

wherein $R^9$ represents a hydrogen atom or an organic group, and $R^{c1}$ to $R^{c5}$ represent a hydrogen atom, a halogen atom, or an organic group, and
wherein the insertion auxiliary tube is designed such that at least a part of the endoscope can be inserted through the insertion auxiliary tube and into a body cavity.

2. The combination according to claim 1, wherein $R^a$ represents a group represented by formula (5) below or a nitrogen-containing organic group, Formula (5)

wherein n2 represents 1 to 10,000, $R^{10}$ represents a hydrogen atom or an organic group, and * represents a direct bond.

3. The combination according to claim 1, wherein n1 represents 135 to 10,000.

4. The combination according to claim 1,
wherein the polymer of the layer b is a crosslinked body, and
the crosslinked body comprises the polymer and a crosslinked structure that crosslinks the polymer, wherein the crosslinked structure is derived from at least one of a crosslinking agent polymer component comprising a structural unit represented by formula (6) below or a crosslinking agent component represented by formula (7) below, Formula (6)

Formula (7)

wherein $R^{11}$ represents a hydrogen atom or an organic group,

X represents a hydroxy group, a carboxy group, an amino group, an isocyanate group, an oxazolinyl group, an epoxy group, a vinyl group, an ethynyl group, a sulfanyl group, an azide group, a trialkoxysilyl group, or a group having an acid anhydride structure, Y represents an m-valent linking group, m represents an integer of 2 or more, and $R^{dm}$ has the same definition as X.

5. The combination according to claim 4, wherein a content of the crosslinked structure in the crosslinked body of the layer b is 30 to 90 mass %.

6. The combination according to claim 1, wherein a surface of the layer b on an opposite side with respect to the tubular substrate a is subjected to hydrophilic treatment.

7. The combination according to claim 1, wherein the tubular substrate a is formed of at least one of a urethane resin, a silicone resin, a fluorocarbon resin, an olefin resin, or an acrylic resin.

8. The combination according to claim 1, wherein the tubular substrate a is formed of a silicone resin.

9. The combination according to claim 1, wherein the tubular substrate a has a Shore A hardness of A40 or more and less than A95.

10. The combination according to claim 1, wherein the insertion auxiliary tube further comprises a layer c disposed on the layer b, wherein layer c comprises a hydrophilic polymer.

11. The combination according to claim 1, wherein the insertion auxiliary tube has a Shore A hardness of A40 or more and less than A95.

12. The combination according to claim 1, wherein the insertion auxiliary tube has an outer diameter of 7 to 20 mm.

13. The combination according to claim 1, wherein the insertion auxiliary tube has a smaller length than an insertion part of the endoscope, a difference in length between the insertion auxiliary tube and the insertion part of the endoscope is 200 to 800 mm, and the insertion part of the endoscope is a part of the endoscope that is designed to be inserted into the body cavity.

14. The combination according to claim 1, wherein the endoscope is designed to be inserted into the body cavity by rotating the insertion auxiliary tube.

15. A method for producing the combination of the insertion auxiliary tube and the endoscope according to claim 1, the method comprising:

producing the insertion auxiliary tube by a step of applying, onto the tubular substrate a, a composition that includes the polymer and an organic solvent, and a step of combining the insertion auxiliary tube thus produced with the endoscope.

\* \* \* \* \*